(12) United States Patent
Satomi (10) Patent No.: US 12,167,930 B2
(45) Date of Patent: Dec. 17, 2024

(54) BIOLOGICAL SOUND ACQUISITION DEVICE

(71) Applicant: AIR WATER BIODESIGN INC., Kobe (JP)

(72) Inventor: Shunichi Satomi, Osaka (JP)

(73) Assignee: AIR WATER BIODESIGN INC., Kobe (JP)

(*) Notice: Subject to any disclaimer, the term of this patent is extended or adjusted under 35 U.S.C. 154(b) by 150 days.

(21) Appl. No.: 17/914,672

(22) PCT Filed: Mar. 19, 2021

(86) PCT No.: PCT/JP2021/011355
§ 371 (c)(1),
(2) Date: Sep. 26, 2022

(87) PCT Pub. No.: WO2021/193425
PCT Pub. Date: Sep. 30, 2021

(65) Prior Publication Data
US 2023/0125092 A1  Apr. 27, 2023

(30) Foreign Application Priority Data
Mar. 27, 2020  (JP) ................. 2020-057855

(51) Int. Cl.
*A61B 7/04* (2006.01)
*H04R 1/28* (2006.01)
*H04R 1/46* (2006.01)
*H04R 5/00* (2006.01)

(52) U.S. Cl.
CPC ............. *A61B 7/04* (2013.01); *H04R 1/2892* (2013.01); *H04R 1/46* (2013.01)

(58) Field of Classification Search
CPC .......... A61B 7/04; H04R 1/2892; H04R 1/46
USPC ..................................................... 381/67, 28
See application file for complete search history.

(56) References Cited

U.S. PATENT DOCUMENTS

| | | | |
|---|---|---|---|
| 5,492,129 | A | 2/1996 | Greenberger |
| 5,883,339 | A | 3/1999 | Greenberger |
| 7,998,091 | B2 | 8/2011 | Carim et al. |
| 8,333,718 | B2 | 12/2012 | Carim et al. |

(Continued)

FOREIGN PATENT DOCUMENTS

| | | |
|---|---|---|
| JP | 2000060845 A | 2/2000 |
| JP | 2009517129 A | 4/2009 |

(Continued)

OTHER PUBLICATIONS

International Search Report for related Application No. PCT/JP2021/011355, mailed Jun. 1, 2021, 2 pages.

(Continued)

*Primary Examiner* — Ammar T Hamid
(74) *Attorney, Agent, or Firm* — Procopio, Cory, Hargreaves & Savitch LLP (57) ABSTRACT

A biological sound acquisition device (10) includes a housing (100), a first acceleration sensor (210), and a second acceleration sensor (220). The first acceleration sensor (210) is disposed in the housing (100). The first acceleration sensor (210) is mechanically connected to the housing (100) through a first vibration damping member (410). The second acceleration sensor (220) is disposed in the housing (100).

8 Claims, 11 Drawing Sheets

(56) References Cited

U.S. PATENT DOCUMENTS

2007/0113654 A1    5/2007  Carim et al.
2011/0301503 A1   12/2011  Carim et al.
2018/0082672 A1*   3/2018  Murata ................... H04R 5/04
2019/0216420 A1    7/2019  Hsu et al.

FOREIGN PATENT DOCUMENTS

| JP | 2013074916 A | | 4/2013 |
| JP | 2014045917 A | * | 3/2014 |
| JP | 2016129635 A | | 7/2016 |
| JP | 2017023595 A | | 2/2017 |
| WO | 2019/017378 A1 | | 1/2019 |

OTHER PUBLICATIONS

Extended European Search Report received in EP Application No. 21774110.7, dated Mar. 6, 2024, in 8 pages.

* cited by examiner

BIOLOGICAL SOUND ACQUISITION DEVICE

CROSS-REFERENCE TO RELATED APPLICATIONS

This application is a U.S. National Stage entry of PCT Application No: PCT/JP2021/011355 filed Mar. 19, 2021, which claims priority to Japanese Patent Application No. 2020-057855, filed Mar. 27, 2020, the contents of which are incorporated herein by reference.

TECHNICAL FIELD

The present invention relates to a biological sound acquisition device.

BACKGROUND ART

Recently, various biological sound acquisition devices used in biological sound stethoscopes such as electronic stethoscopes have been developed. The biological sound acquisition device may acquire not only biological sounds but also external noise. Accordingly, the biological sound acquisition device is required to suppress the external noise.

Patent Document 1 describes a structure for suppressing external noise in a biological sound acquisition device. In this structure, a sensor module is supported by a main body portion by a damper portion. In the structure, even when noise propagates from the main body portion to the sensor module through the damper portion, the damper portion suppresses the noise from propagating.

RELATED DOCUMENT

Patent Document

Patent Document 1: JP-A-2017-23595

SUMMARY OF THE INVENTION

Technical Problem

A biological sound acquisition device is required to suppress external noise. In order to suppress the external noise, a sensor may be supported by a damper, for example as described in Patent Document 1. However, simply supporting the sensor by the damper may not be sufficient to suppress the external noise.

One example of problems to be solved by the present invention is to suppress external noise in a biological sound acquisition device.

Solution to Problem

The invention according to claim 1 is a biological sound acquisition device including:
a housing;
a first acceleration sensor disposed within the housing and mechanically connected to the housing through a first vibration damping member; and
a second acceleration sensor disposed within the housing.
The invention according to an exemplary aspect is a biological sound acquisition device including:
a housing;
a first vibration sensor disposed within the housing and mechanically connected to the housing through a first vibration damping member; and
a second vibration sensor disposed within the housing.

DESCRIPTION OF EMBODIMENTS

Hereinafter, an embodiment of the present invention will be described with reference to the drawings. In all the drawings, the same constituent elements are denoted by the same reference numerals, and descriptions thereof will not be repeated.

Figure 1:
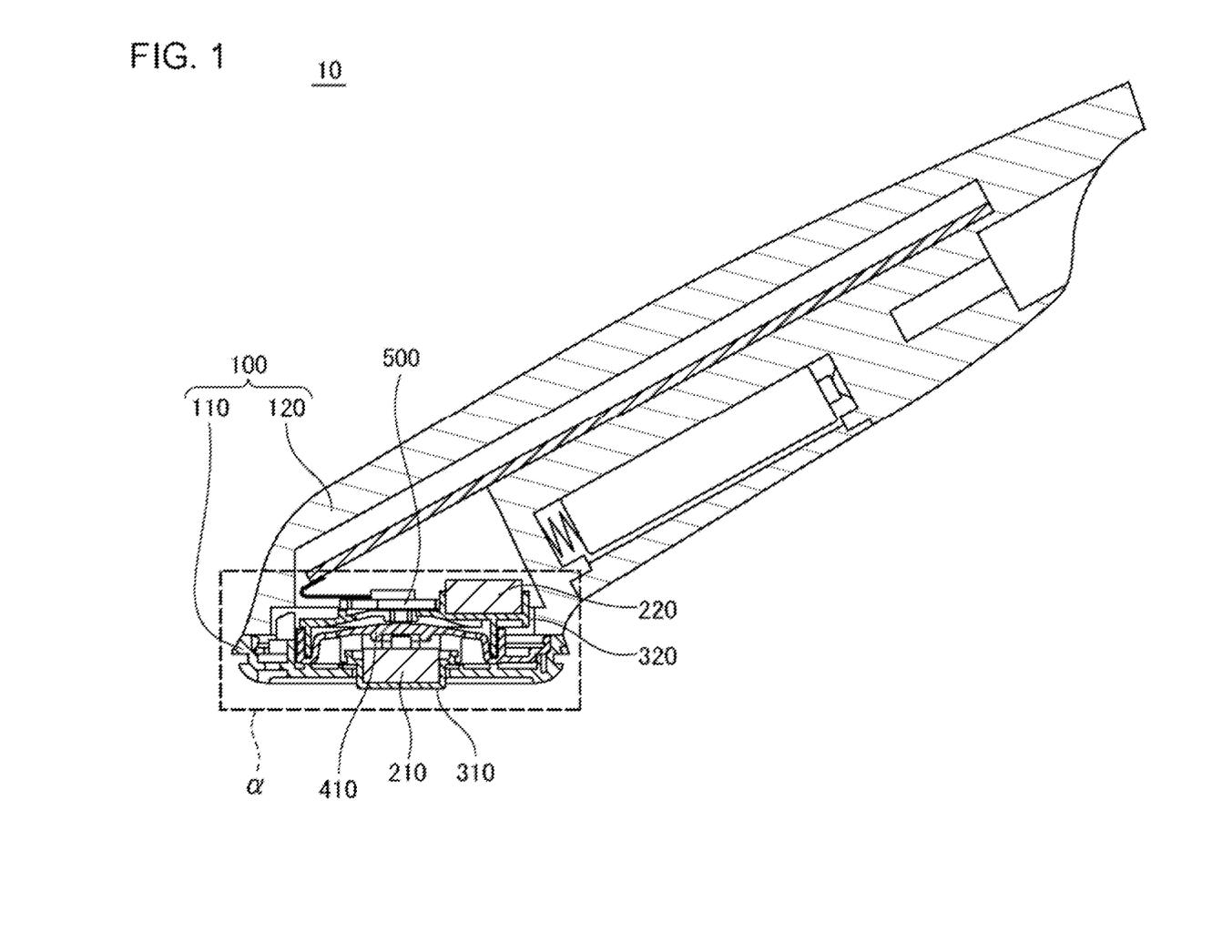
FIG. 1 is a cross-sectional view of a biological sound acquisition device according to an embodiment.
Figure 2:
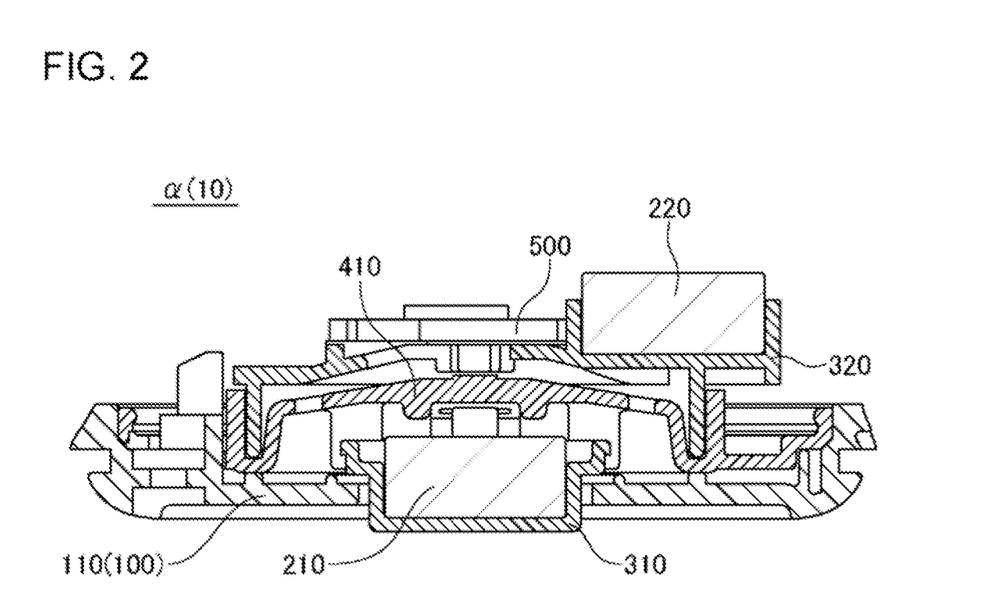
FIG. 2 is an enlarged view of a region α shown in FIG. 1.
Figure 3:
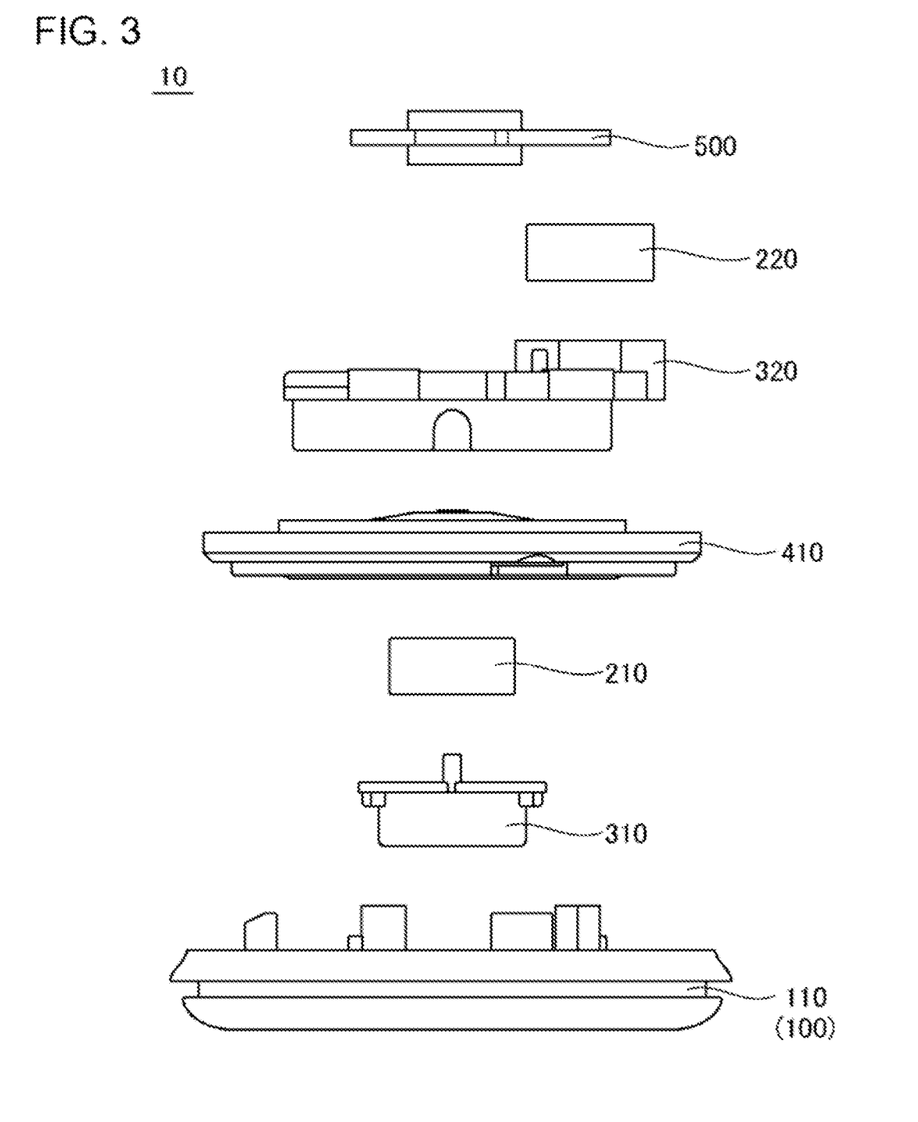
FIG. 3 is an exploded view of the biological sound acquisition device shown in FIG. 1.

FIG. 1 is a cross-sectional view of a biological sound acquisition device 10 according to an embodiment. FIG. 2 is an enlarged view of a region α shown in FIG. 1. FIG. 3 is an exploded view of the biological sound acquisition device 10 shown in FIG. 1. FIGS. 1 and 2 show cross sections passing through a center of a first housing member 110, which will be described later, along a height direction of the first housing member 110. FIGS. 2 and 3 do not show a second housing member 120 of FIG. 1.

The biological sound acquisition device 10 acquires a biological sound, that is, a biological vibration. The biological sound or biological vibration in the present embodiment is emitted as a vibration when a sound or vibration generated in a body of a measurement object is propagated through a subcutaneous tissue of the measurement object, and the biological sound or biological vibration in the present embodiment is emitted as a sound when the sound or vibration generated in the body of the measurement object propagates to outside air. For example, the biological sound acquisition device 10 acquires a vibration appearing on a body surface of the measurement object.

The biological sound acquisition device 10 includes a housing 100, a first acceleration sensor 210, a second acceleration sensor 220, a first holder 310, a second holder 320, a first vibration damping member 410, and a substrate 500.

The housing 100 has a first housing member 110 and a second housing member 120. The first housing member 110 is a lower member of the housing 100, that is, a base. The second housing member 120 is an upper member of the housing 100. The first acceleration sensor 210, the first holder 310, the second acceleration sensor 220, the second holder 320, the first vibration damping member 410, and the substrate 500 are disposed inside housing 100. As shown in FIGS. 1 and 3, in the present embodiment, the first housing member 110, the first holder 310, the first acceleration sensor 210, the first vibration damping member 410, the second holder 320, the second acceleration sensor 220, the substrate 500, and the second housing member 120 overlap in this order.

The first acceleration sensor 210 is accommodated In the first holder 310. When the biological sound acquisition device 10 acquires a biological sound, the first holder 310 contacts a measurement object such as skin tissue through a biocompatible material such as silicone. The first acceleration sensor 210 is a uniaxial acceleration sensor. The first acceleration sensor 210 is capable of detecting a vibration in a uniaxial direction. In the present embodiment, the first acceleration sensor 210 is capable of detecting a vibration in a direction substantially orthogonal to a tangential plane of the measurement object. The first acceleration sensor 210 may be a multi-axis acceleration sensor, such as a three-axis acceleration sensor.

The second acceleration sensor 220 is accommodated inside the second holder 320. When the biological sound acquisition device 10 acquires a biological sound, the second holder 320 is spaced apart from the measurement object such as the skin tissue. That is, when the biological sound acquisition device 10 acquires biological sounds, the second holder 320 is not in contact with the measurement object such as the skin tissue. The second acceleration sensor 220 is a uniaxial acceleration sensor. The second acceleration sensor 220 can detect a vibration in one axial direction. In the present embodiment, the second acceleration sensor 220 is capable of detecting vibration in a direction substantially orthogonal to the tangential plane of the measurement object. The second acceleration sensor 220 may be a multi-axis acceleration sensor, such as a three-axis acceleration sensor.

A sensitivity axis of the first acceleration sensor 210 and a sensitivity axis of the second acceleration sensor 220 are substantially parallel to each other. The "substantially parallel" means not only the sensitivity axis of the first acceleration sensor 210 and the sensitivity axis of the second acceleration sensor 220 being strictly parallel to each other, but also one of the sensitivity axis of the first acceleration sensor 210 and the sensitivity axis of the second acceleration sensor 220 being inclined within a range of ±15 degrees with respect to the other of the sensitivity axis of the first acceleration sensor 210 and the sensitivity axis of the second acceleration sensor 220. In this case, as will be described later, the noise included in the detection signal detected by the first acceleration sensor 210 and the noise included in the detection signal detected by the second acceleration sensor 220 can be at least partially canceled by calculating a difference between the detection signal detected by the first acceleration sensor 210 and the signal detected by the second acceleration sensor 220. The sensitivity axis of the first acceleration sensor 210 is an axis along which the first acceleration sensor 210 is capable of detecting the vibration. Similarly, the sensitivity axis of the second acceleration sensor 220 is an axis along which the second acceleration sensor 220 is capable of detecting the vibration.

Even if the sensitivity axis of the first acceleration sensor 210 and the sensitivity axis of the second acceleration sensor 220 are not parallel to each other but a noise component included in a detection result of the first acceleration sensor 210 and a noise component included in a detection result of the second acceleration sensor 220 is extractable by signal processing of the detection result of the first acceleration sensor 210 and the detection result of the second acceleration sensor 220, the noise included in the detection signal detected by the first acceleration sensor 210 and the noise included in the detection signal detected by the second acceleration sensor 220 can be at least partially canceled using the extracted noise component.

The first vibration damping member 410 is, for example, a viscoelastic body such as a damper. Depending on hardness of the first vibration damping member 410, the first vibration damping member 410 functions as a low-pass filter to block relatively high frequency vibrations and to pass relatively low frequency vibrations.

The first acceleration sensor 210 is mechanically connected to housing 100 through the first vibration damping member 410. For example, the first acceleration sensor 210 being mechanically connected to the housing 100 through the first vibration damping member 410 means that the first acceleration sensor 210 is disposed with respect to the first vibration clamping member 410 such that a vibration of a predetermined frequency of the first acceleration sensor 210, such as a noise propagated from the housing 100 is damped by the first vibration damping member 410. For example, the first acceleration sensor 210 or the first holder 310 that accommodates the first acceleration sensor 210 may be in contact with the first vibration damping member 410. For example, the first acceleration sensor 210 being mechanically connected to the housing 100 through the first vibration damping member 410 may mean that the first acceleration sensor 210 is elastically connected to the housing 100 through the first vibration damping member 410.

Since the first acceleration sensor 210 is mechanically connected to the housing 100 through the first vibration damping member 410, the first acceleration sensor 210 is vibrated due to the biological sound as if the first acceleration sensor 210 is separated from the housing 100 by the first vibration damping member 410 when the biological sound propagates to the first holder 310. Generally, according to the second law of motion, an acceleration of an acceleration sensor decreases as a mass of a vibrating object increases when a force of vibration is constant. Accordingly, the vibration of the housing 100 along with the first acceleration sensor 210 due to biological vibrations may lead to loss or reduction of biological vibrations. In contrast, according to the present embodiment, the first vibration damping member 410 can suppress the loss or reduction of the biological vibration, and the biological vibration can be accurately detected by the first acceleration sensor 210.

The second acceleration sensor 220 is mechanically connected to the housing 100 without through the first vibration damping member 410. For example, the second acceleration sensor 220 being mechanically connected to the housing 100 without through the first vibration damping member 410 means that the second acceleration sensor 220 is disposed with respect to the first vibration damping member 410 such that the vibration of a predetermined frequency of the second acceleration sensor 220, such as the noise propagated from the housing 100 is not damped by the first vibration damping member 410. For example, the second acceleration sensor 220 being mechanically connected to the housing 100 without through the first vibration damping member 410 may mean that the second acceleration sensor 220 is rigidly connected to the housing 100 without through the first vibration damping member 410.

Figure 4:
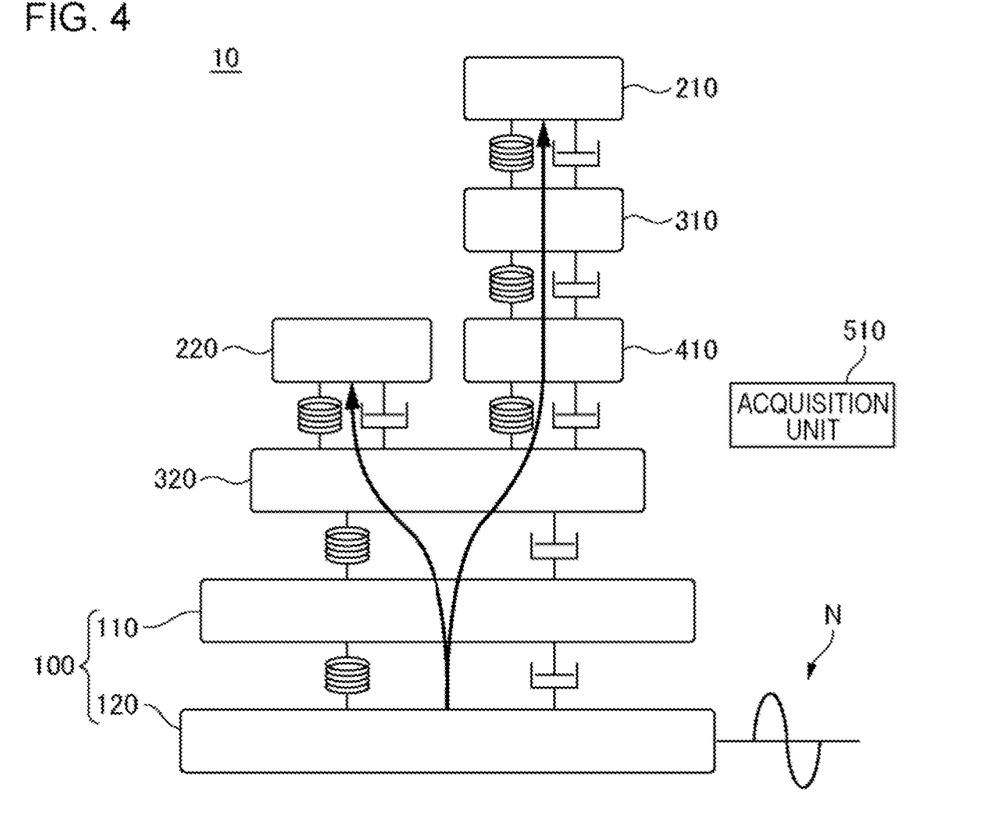
FIG. 4 is a diagram showing a multi-mass model for explaining propagation of external noise in the biological sound acquisition device according to the embodiment.

FIG. 4 is a diagram showing a multi-mass model for explaining propagation of external noise in the biological sound acquisition device 10 according to the embodiment. An acquisition unit 510 shown in FIG. 4 is shown as a functional block diagram. The acquisition unit 510 is implemented, for example, by an integrated circuit mounted on substrate 500 shown in FIGS. 1 to 3.

In this model, first, a noise N as the external noise propagates to the second housing member 120. The noise N is, for example, a muscle sound noise generated from a hand holding the second housing member 120. The muscle sound noise is a sound generated by muscle activity in a human body such as hands.

As indicated by an arrow extending from the second housing member 120 to the first acceleration sensor 210 through the first housing member 110, the second holder 320, the first vibration damping member 410, and the first holder 330, the noise N propagated to the second housing member 120 reaches the first acceleration sensor 210 from the second housing member 120 through the first housing member 110, the second holder 320, the first vibration damping member 410, and the first holder 310. In this case, the first acceleration sensor 210 detects the noise N filtered by the first vibration damping member 410 for a certain frequency.

The first vibration damping member 410 blocks a relatively high frequency component of the noise N. Accordingly, in order to block the noise N over a wide frequency band by the first vibration damping member 410, it is desirable to set the natural frequency of the first vibration damping member 410 to a low frequency. However, there is a limit to how low the natural frequency of the first vibration damping member 410 can be set for the following reasons. That is, the natural frequency of the first vibration damping member 410 is represented by $(k/m)^{1/2}/2\pi$. Here, k is a spring constant of the first vibration damping member 410 and m is a mass of the first acceleration sensor 210 and the first holder 310 supported by the first vibration damping member 410. The natural frequency decreases as the mass m increases. However, as the mass m increases, a loss or reduction of biological vibration due to the weight of the first acceleration sensor 210 and the first holder 310 increases. Accordingly, the first vibration damping member 410 alone cannot, sufficiently remove a relatively low frequency component of the noise N. In the present embodiment, as will foe described later, the relatively low frequency component of the noise N can be removed by using the detection result of the second acceleration sensor 220.

As indicated by an arrow extending from the second housing member 120 to the second acceleration sensor 220 through the first housing member 110 and the second holder 320, the noise N propagated to the second housing member 120 reaches the second acceleration sensor 220 from the second housing member 120 through the first housing member 110 and the second holder 320.

The acquisition unit 510 acquires a difference between the detection signal detected by the first acceleration sensor 210 and the detection signal detected by the second acceleration sensor 220. Specifically, each detection signal of the first acceleration sensor 210 and the second acceleration sensor 220 is output as an electrical signal. The acquisition unit 510 calculates a difference between the electrical signal output from the first acceleration sensor 210 and the electrical signal output from the second acceleration sensor 220. This can remove a component of the noise N that cannot be sufficiently removed by the first vibration damping member 410 alone, that is, a relatively low frequency component of the noise N.

When the noise N is reduced by the difference between the detection signal detected by the first acceleration sensor 210 and the detection signal detected by the second acceleration sensor 220, a level and a phase of the electrical signal output from the first acceleration sensor 210, and a level and a phase of the electrical signal output, from the second acceleration sensor 220 are preferably equal or approximate. For example, the level and phase of the electrical signal output from the first acceleration sensor 210 and the level and the phase of the electrical signal output from the second acceleration sensor 220 can be equal or approximate by filtering the electrical signal output from the second acceleration sensor 220 by an electrical filter having filter characteristics equal to or approximate to filter characteristics of the first vibration damping member 410.

Figure 5:
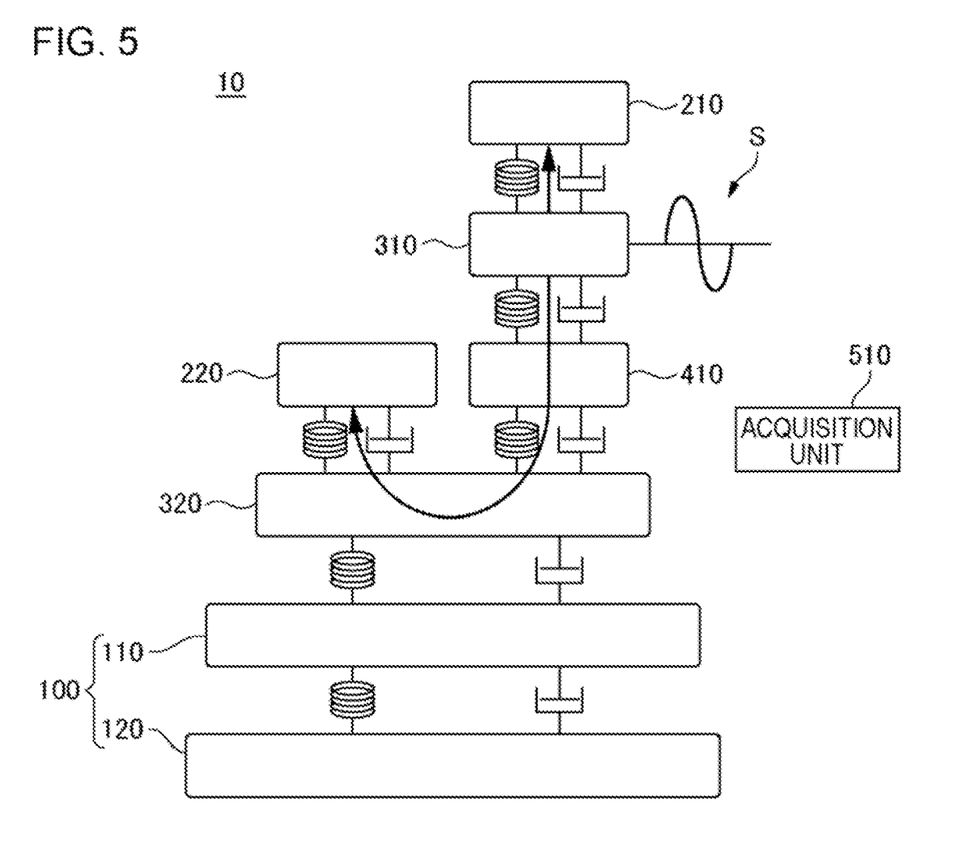
FIG. 5 is a diagram showing a multi-mass model for explaining propagation of a biological sound in the biological sound acquisition device according to the embodiment.

FIG. 5 is a diagram showing a multi-mass model for explaining the propagation of the biological sound in the biological sound acquisition device 10 according to the embodiment.

In this model, first, a biological sound S propagates to the first holder 310.

As indicated by an arrow extending from the first holder 310 to the first acceleration sensor 210, the biological sound S propagated to the first holder 310 reaches the first acceleration sensor 210. The first acceleration sensor 210 detects the biological sound S that reaches the first acceleration sensor 210. That is, the biological sound S propagates to the first acceleration sensor 210 without through the first vibration damping member 410. If the biological sound S propagates to the first acceleration sensor 210 through the first vibration damping member 410, the biological sound S is lost or reduced by first vibration damping member 410. In contrast, in the present embodiment, the biological sound S propagating to the first acceleration sensor 210 can be prevented from being lost or reduced by the first vibration damping member 410.

As indicated by an arrow extending from the first holder 310 to the second acceleration sensor 220 through the first vibration damping member 410 and the second holder 320, the biological sound S propagated to the first holder 310 reaches the second acceleration sensor 220 through the first vibration damping member 410 and the second holder 320. The second acceleration sensor 220 detects the biological sound S that reach the second acceleration sensor 220. That is, the biological sound S propagates to the second acceleration sensor 220 through the first vibration damping member 410. Accordingly, the biological sound S propagating to the second acceleration sensor 220 can be lost or reduced by the first vibration damping member 410.

From the perspective that the biological sound S propagated to the first holder 310 propagates to the second acceleration sensor 220 to reduce the attenuation or loss of the biological sound S detected by the first acceleration sensor 210, a total mass of the second acceleration sensor 220, the second holder 320, and the biological sound acquisition device 10 including the housing 100 except the first acceleration sensor 210 and the first holder 310 may be sufficiently large relative to a total mass of the first acceleration sensor 210 and the first holder 310. More specifically, a mass of the second acceleration sensor 220 and the second holder 320 including the housing 100 may be 30 times or more a mass of the first acceleration sensor 210 and the first holder 310.

Figure 6:
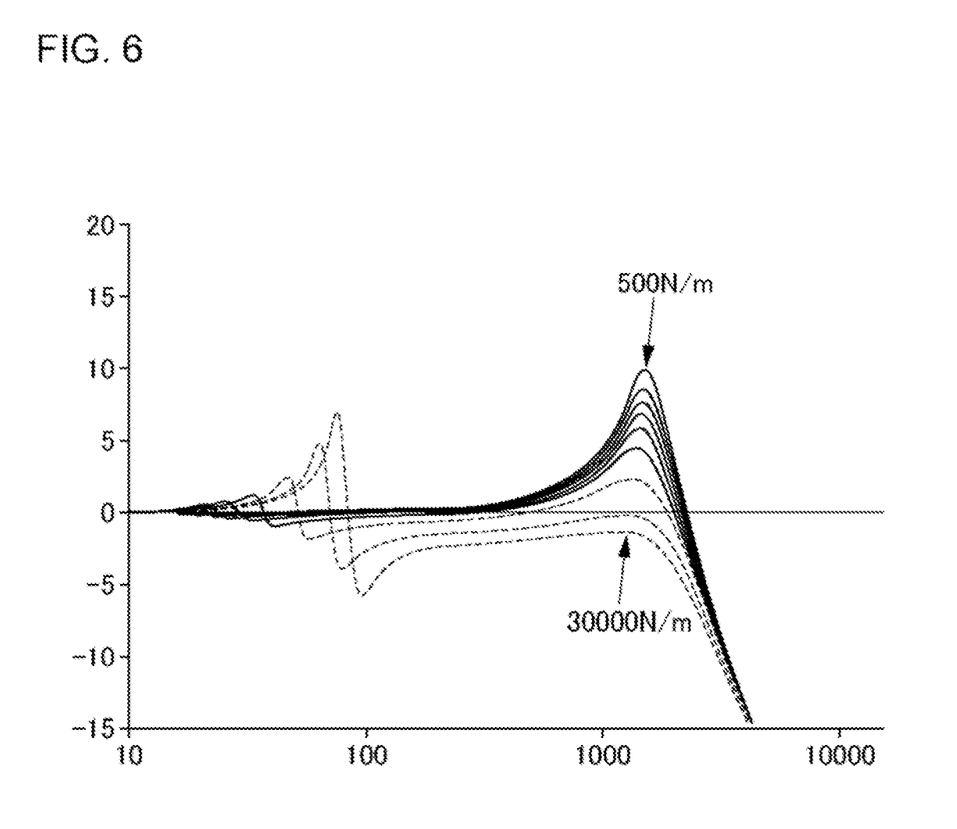
FIG. 6 is a graph showing frequency characteristics of a relative acceleration detected by a first acceleration sensor of the biological sound acquisition device according to the embodiment relative to a biological vibration as an input signal.

FIG. 6 is a graph showing the frequency characteristics of the relative acceleration detected by the first acceleration sensor 210 of the biological sound acquisition device 10 according to the embodiment relative to the biological vibration as the input signal.

In FIG. 6, a horizontal axis of the graph indicates a vibration frequency [Hz]. A vertical axis of the graph indicates a relative acceleration [dB] detected by the first acceleration sensor 210 relative to the biological vibration as the input signal. The graph shows the frequency characteristics of the first vibration damping member 410 at nine spring constants. Peaks in a frequency band of 1,000 Hz to 10,000 Hz for the nine frequency characteristics decrease in the order of 500 N/m, 1,000 N/m, 1,500 N/m, 2,000 N/m, 3,000 N/m, 5,000 N/m, 10,000 N/m, 20,000 N/m, and 30,000 N/m for the spring constant.

In the graph in FIG. 6, the simulation was conducted under the following conditions.

(Mass)
Measurement object: 0.2 kg
First acceleration sensor 210: 0.001 kg
Second acceleration sensor 220: 0.001 kg
Second housing member 120: 0.1 kg (Spring Constant)
Measurement object: 1000 N/m
First acceleration sensor 210: 100,000 N/m
Second acceleration sensor 220: 100,000 N/m
Second housing member 120: 3,000 N/m (Attenuation Coefficient)
Measurement object: 4.242641 Ns/m
First acceleration sensor 210: 2 Ns/m
Second acceleration sensor 220: 2 Ns/m
Second housing member 120: 14.69694 Ns/m This simulation assumes that the measurement object is a skin tissue. In general, the skin tissue is referred to as a soft elastic body, and when the skin tissue is pushed at the same area and the same pushing amount, a reaction force from the skin tissue is different between a thick portion and a thin portion of the skin tissue. The simulation assumes a skin tissue thickness of 4.5 mm. The spring constant of 4.5 mm thick skin tissue is estimated to be approximately 1,000 N/m.

As shown in the graph of FIG. 6, resonance and anti-resonance of the frequency characteristics are relatively prominent at the frequency of 100 Hz or less as the spring constant increases, especially at the spring constants of 30,000 N/m, 20,000 N/m, and 10,000 N/m where the frequency characteristics are indicated by dashed lines. The peak of the frequency characteristic at a frequency of 1,000 Hz or wore decreases as the spring constant increases, especially at spring constants of 30,000 N/m, 20,000 N/m, and 10,000 N/m where the frequency characteristics are indicated by the dashed lines. This suggests that a sensing target of the first acceleration sensor 210 shifts from the vibration of the skin tissue to the vibration of the second housing member 120 as the first vibration damping member 410 hardens.

From the graph of FIG. 6, when the spring constant of the first vibration damping member 410 is equal, to or less than the spring constant of the skin tissue, that is, the spring constant of the measurement object, the resonance, that is, the peak of the relative acceleration greater than 0 dB, and anti-resonance, that is, the peak of the relative acceleration less than 0 dB in the frequency characteristic at the frequency of 100 Hz or less, hardly appear, and the peak of the frequency characteristic at the frequency of 1,000 Hz or more appears relatively prominently. The resonance and the anti-resonance at the frequency of 1,000 Hz or less in the graph of FIG. 6 are due to the natural frequency of the housing 100. When the natural frequency of first vibration damping member 410, that is, the natural frequency approaches the natural frequency of housing 100, the housing 100 and the first vibration damping member 410 are likely to resonating with each other. Accordingly, in order to suppress mutual resonance between the housing 100 and the first vibration damping member 410, it is preferred that the natural frequency of the first vibration damping member 410 is lower than the natural frequency of the housing 100. Furthermore, it is preferred that a resonance frequency band of the housing 100 and a resonance frequency band of the first vibration damping member 410 do not overlap.

(Variant 1)

Figure 7:
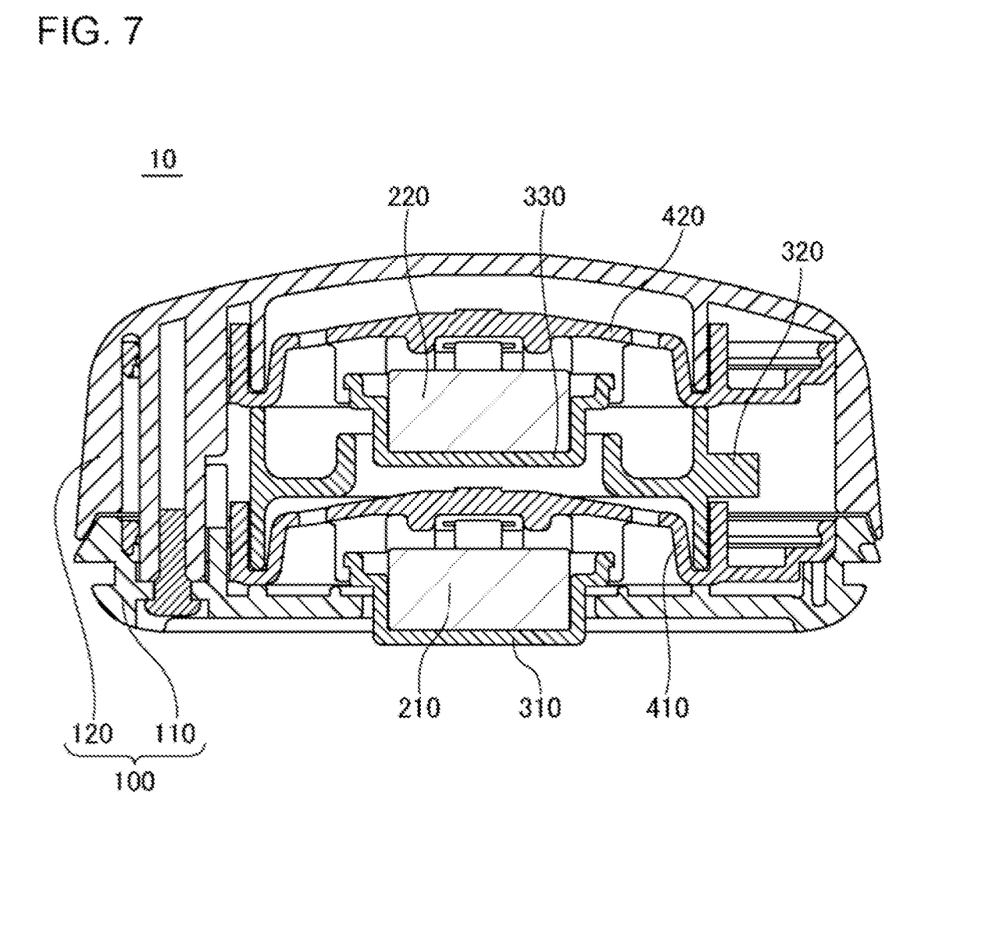
FIG. 7 is a cross-sectional view of a biological sound acquisition device according to Variant 1.
Figure 8:
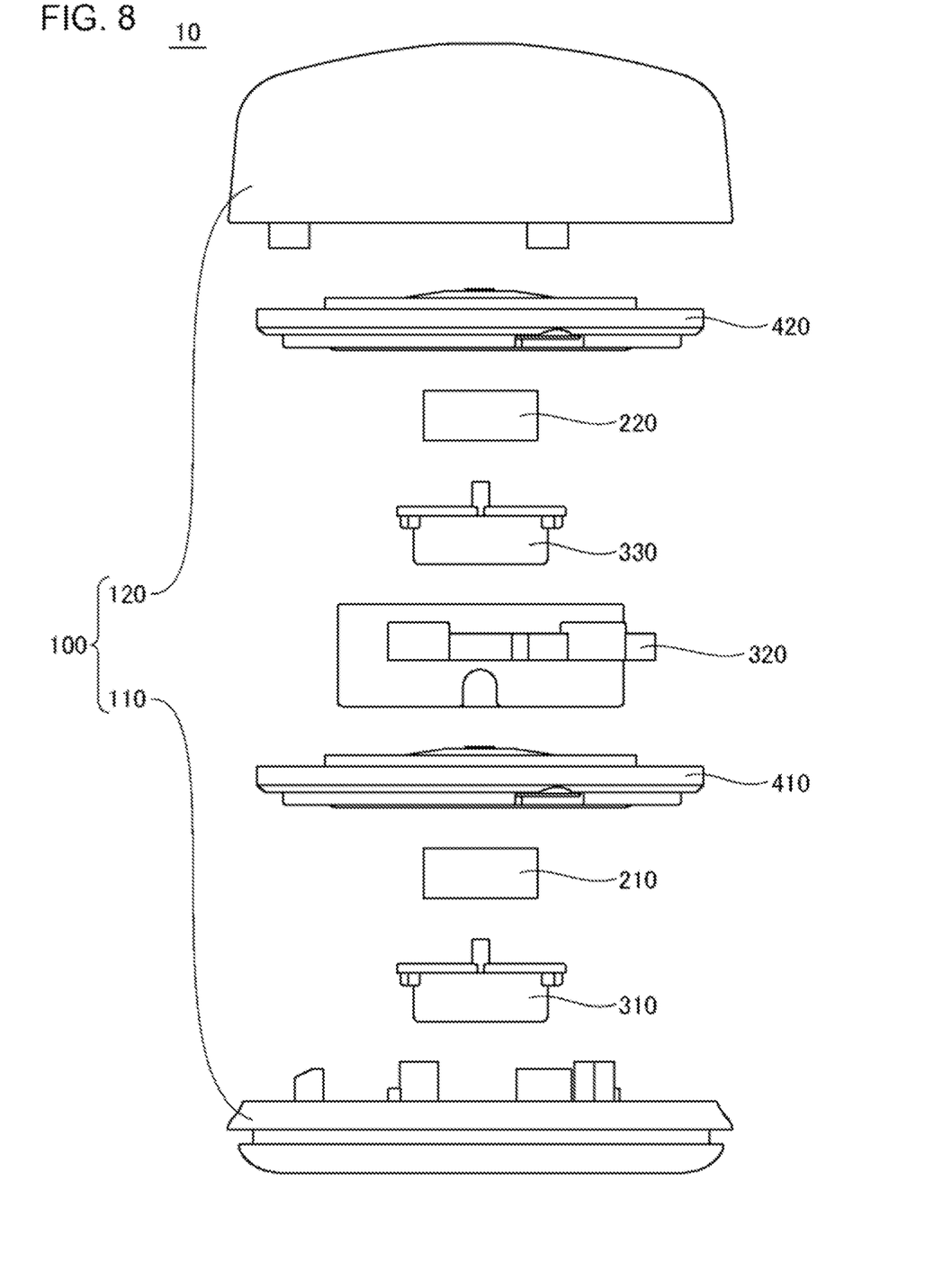
FIG. 8 is an exploded view of the biological sound acquisition device shown in FIG. 7.

FIG. 7 is a cross-sectional view of a biological sound acquisition device 10 according to Variant 1. FIG. 8 is an exploded view of the biological sound acquisition device 10 shown in FIG. 7. FIG. 7 shows a cross section passing through a center of the housing 100 along a height direction of the housing 100. The biological sound acquisition device 10 according to Variant 1 is the same as the biological sound acquisition device 10 according to the embodiment except for the following points.

The biological sound acquisition device 10 further includes a second vibration damping member 420 and a third holder 330. The second vibration damping member 420 is, for example, a viscoelastic body such as a damper. As shown in FIG. 8, the first housing member 110, the first holder 310, the first acceleration sensor 210, the first vibration damping member 410, the second holder 320, the third holder 330, the second acceleration sensor 220, the second vibration dancing member 420, and the second housing member 120 overlap in this order. The second acceleration sensor 220 is accommodated in the third holder 330. The second holder 320 is mechanically connected to the housing 100.

The second acceleration sensor 220 is mechanically connected to the housing 100 through the second vibration damping member 420. For example, the second acceleration sensor 220 being mechanically connected to the housing 100 through the second vibration damping member 420 means that the second acceleration sensor 220 is disposed with respect, to the second vibration damping member 420 such that the vibration of a predetermined frequency of the second acceleration sensor 220, such as the noise propagated from the housing 100 is damped by the second vibration damping member 420. For example, the second acceleration sensor 220 or the second holder 320 that accommodates the second acceleration sensor 220 may be in contact with the second vibration damping member 420. For example, the second acceleration sensor 220 being mechanically connected to the housing 100 through the second vibration damping member 420 may mean that the second acceleration sensor 220 is elastically connected to the housing 100 through the second vibration damping member 420.

Figure 9:
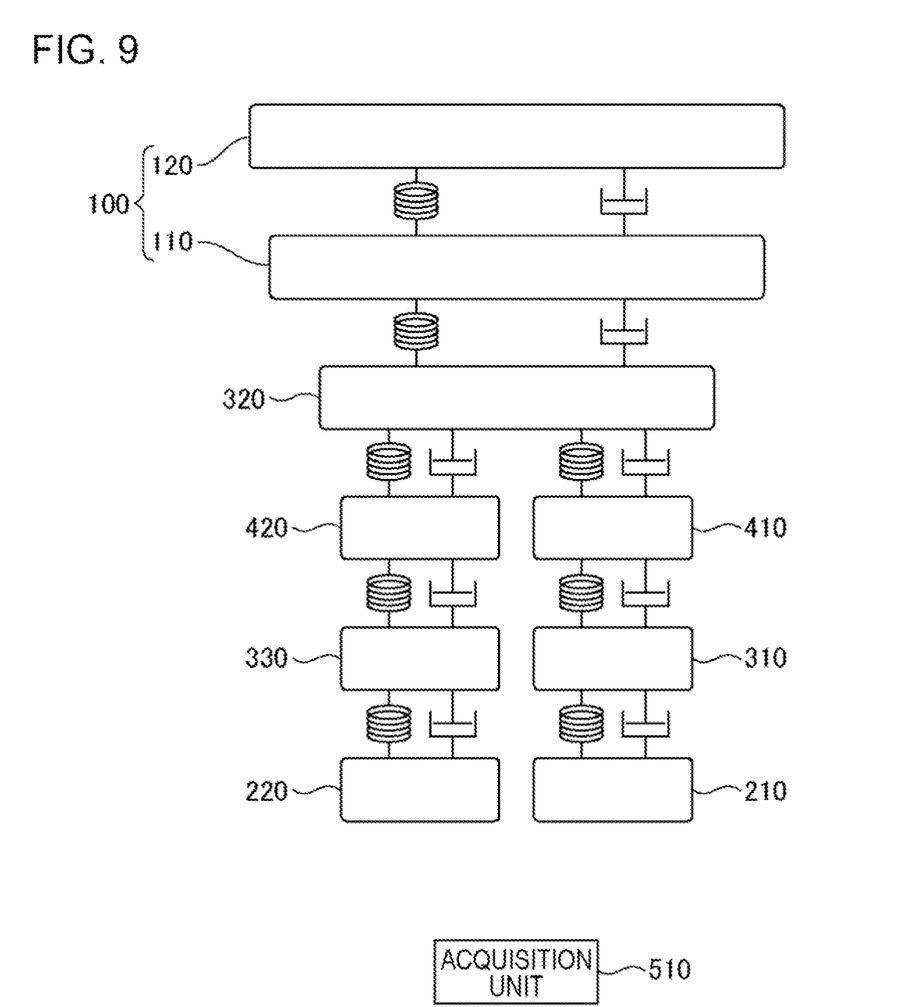
FIG. 9 is a diagram showing a multi-mass model of the biological sound acquisition device according to Variant 1.

FIG. 9 is a diagram showing a multi-mass model of the biological sound acquisition device 10 according to Variant 1.

When the noise such as the muscle sound noise propagates to the second housing member 120, the noise reaches the first acceleration sensor 210 from the second housing member 120 through the first housing member 110, the second holder 320, the first vibration damping member 410, and the first holder 310, and the noise reaches the second acceleration sensor 220 from the second housing member 120 through the first housing member 110, the second holder 320, the second vibration damping member 420, and the third holder 330.

As in the embodiment, the acquisition unit 510 acquires the difference between the detection signal detected by the first acceleration sensor 210 and the detection signal detected by the second acceleration sensor 220. In the present variant, a mass system from the second housing member 120 to the first acceleration sensor 210 and a mass system from the first acceleration sensor 210 to the second acceleration sensor 220 are the same or similar as each other. Accordingly, the noise detected by the first acceleration sensor 210 and the noise detected by the second acceleration sensor 220 can be at least partially canceled in the entire frequency band of the biological sounds, such as 20 Hz to 2 kHz.

When the biological sound propagates to the first holder 310, the biological sound propagates from the first holder 310 to the first acceleration sensor 210, and reaches the second acceleration sensor 220 from the first holder 310 through the first vibration damping member 410, the second holder 320, the second vibration damping member 420, and the third holder 330. That is, the biological sound propagates to the first acceleration sensor 210 without through the first vibration damping member 410 and the second vibration damping member 420. On the other hand, the biological sound propagates to the second acceleration sensor 220 through the first vibration damping member 410 and the second vibration damping member 420.

Figure 10:
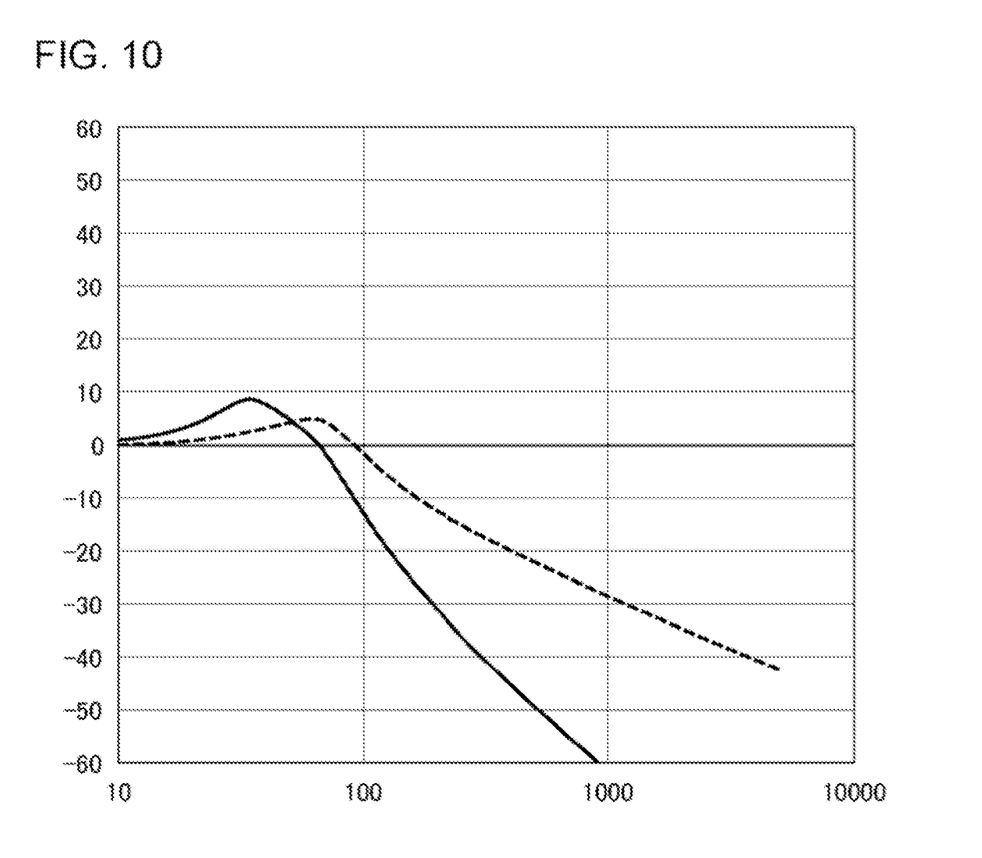
FIG. 10 is a graph showing frequency characteristics of a relative acceleration detected by a second acceleration sensor of the biological sound acquisition device according to Variant 1 relative to the biological vibration as the input signal, and frequency characteristics of a relative acceleration detected by a second acceleration sensor of the biological sound acquisition device according to the embodiment relative to the biological vibration as the input signal.

FIG. 10 is a graph showing the frequency characteristics of the relative acceleration detected by the second acceleration sensor 220 of the biological sound acquisition device 10 according to Variant 1 relative to the biological vibration as the input signal, and the frequency characteristics of the relative acceleration detected by the second acceleration sensor 220 of the biological sound acquisition device 10 according to the embodiment relative to the biological vibration as the input signal.

In FIG. 10, a horizontal axis of the graph indicates a vibration frequency [dB]. A vertical axis of the graph indicates a relative acceleration [dB] detected by the second acceleration sensor 220 relative to the biological vibration as the input signal. A solid line in the graph indicates the frequency characteristics of the relative acceleration detected by the second acceleration sensor 220 of the biological sound acquisition device 10 according to Variant 1 relative to the biological vibrations as the input signal. A dashed line in the graph indicates the frequency characteristics of the relative acceleration detected by the second acceleration sensor 220 of the biological sound acquisition device 10 according to the embodiment relative to the biological vibration as the input signal.

In the embodiment, as shown in FIG. 5, the biological sound reaching the second acceleration sensor 220 from the first holder 310 passes through only one vibration damping member, that is, the first vibration damping member 410. In the present variant, on the other hand, as shown in FIG. 9, the biological sound reaching the second acceleration sensor 220 from the first holder 310 passes through two vibration damping members, that is, the first vibration damping member 410 and the second vibration damping member 420. Accordingly, biological sounds reaching the second acceleration sensor 220 from the first holder 310 can be damped by more vibration damping members in the present variant than in the embodiment.

As shown in FIG. 10, when two vibration damping members are used, the frequency that changes from the resonance frequency band, that is, the frequency band where the relative acceleration is higher than 0 dB, to the anti-resonance frequency band, that is, the frequency band where the relative acceleration is lower than 0 dB is about 65 Hz. When one vibration damping member is used, on the other hand, the frequency that changes from the resonance frequency band to the anti-resonance frequency band is about 91 Hz. Furthermore, when two vibration damping members are used, relative acceleration peaks at about 35 Hz in the resonance frequency band. When one vibration damping member is used, on the other hand, the relative acceleration peaks at about 60 Hz in the resonance frequency band.

As described above, the acquisition unit 510 acquires the difference between the detection signal detected by first acceleration sensor 210 and the detection signal detected by second acceleration sensor 220. Accordingly, in FIG. 10, the loss of the detection signal of the first acceleration sensor 210 for the difference in the frequency band where the relative acceleration is higher than 0 dB is greater than the loss of the detection signal of the first acceleration sensor 210 for the difference in the frequency band where the relative acceleration is lower than 0 dB. From FIG. 10, within the biological sound frequency band, which is regarded as about 20 Hz to 2 kHz, the frequency band where the relative acceleration is higher than 0 dB using two vibration damping members is narrower than the frequency band where the relative acceleration is higher than 0 dB using one vibration damping member. Accordingly, the loss of the detection signal of the first acceleration sensor 210 for the difference using two vibration damping members is smaller than the loss of the detection signal of the first acceleration sensor 210 for the difference using one vibration damping member.

(Variant 2)

Figure 11:
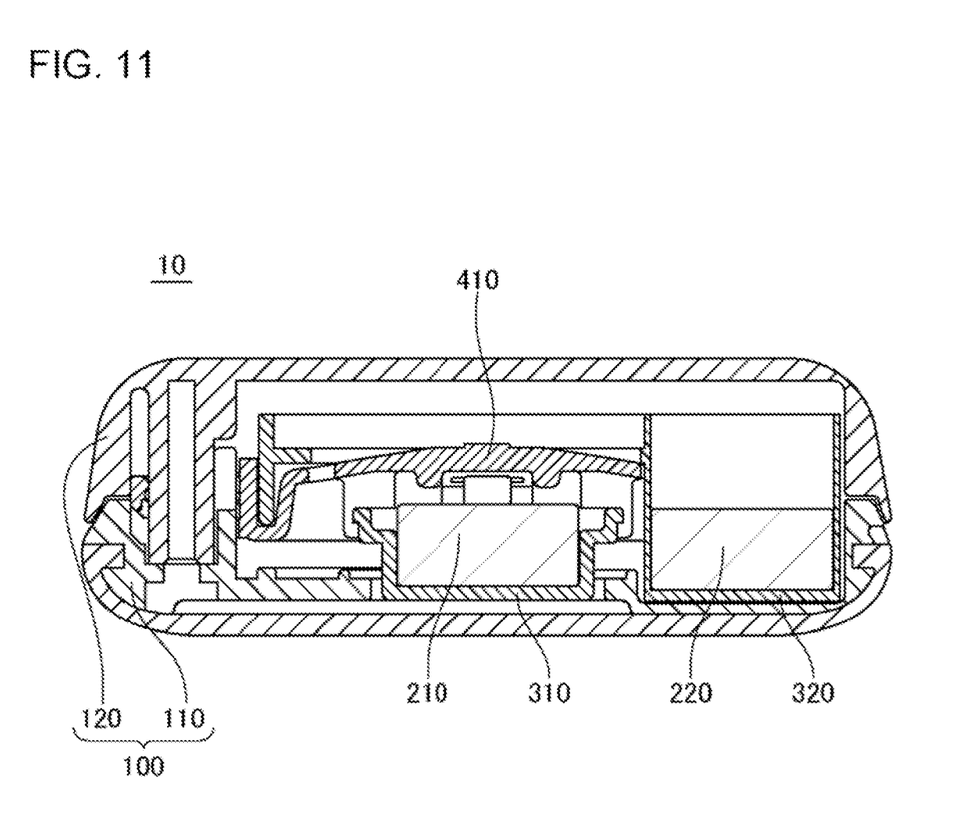
FIG. 11 is a cross-sectional view of a biological sound acquisition device according to Variant 2.

FIG. 11 is a cross-sectional view of a biological sound acquisition device 10 according to Variant 2. FIG. 11 shows a cross section passing through the center of the housing 100 along the height direction of the housing 100. The biological sound acquisition device 10 according to Variant 2 is the same as the biological sound acquisition device 10 according to the embodiment except for the following points.

The first acceleration sensor 210 and the second acceleration sensor 220 are disposed in a direction orthogonal to the height direction of the housing 100. Also in Variant 2, the external noise such as the muscle sound noise can be suppressed in the same manner as in the embodiment.

Although the embodiments and variants have been described above with reference to the drawings, these are examples of the present invention, and various configurations other than those described above can also be adopted.

For example, in the embodiment and variants, the first acceleration sensor 210 and the second acceleration sensor 220 are used as the vibration sensors to detect the biological sound or the noise. However, the vibration sensor may be a vibration sensor different from the acceleration sensor, such as a velocity sensor, for example.

Further, for example, in the embodiment and the variant, the noise N is reduced by calculating the difference between the detection signal detected by the first acceleration sensor 210 and the detection signal detected by the second acceleration sensor 220. However, the detection signal detected by the second acceleration sensor 220 may be filtered before calculating the difference. More specifically, subtraction processing may be performed after applying a high-pass filter to attenuate the signal in the frequency band in which the relative acceleration in FIG. 10 is higher than 0 dB.

This application claims priority based on Japanese Patent Application No. 2020-057855 filed on Mar. 27, 2020, the entire disclosure of which is incorporated herein.

REFERENCE SIGNS LIST 10 biological sound acquisition device
100 housing
110 first housing member
120 second housing member
210 first acceleration sensor
220 second acceleration sensor
310 first holder
320 second holder
330 third folder
410 first vibration damping member
420 second vibration damping member
500 substrate
510 acquisition unit
N noise
S biological sound

The invention claimed is:

1. A biological sound acquisition device comprising:
a housing;
a first acceleration sensor disposed within the housing and mechanically connected to the housing through a first vibration damping member; and
a second acceleration sensor disposed within the housing,
wherein a biological sound propagates to the first acceleration sensor without propagating through the first vibration damping member, and
wherein the biological sound propagates to the second acceleration sensor through the first vibration damping member.

2. The biological sound acquisition device according to claim 1,
wherein a sensitivity axis of the first acceleration sensor and a sensitivity axis of the second acceleration sensor are substantially parallel to each other.

3. The biological sound acquisition device according to claim 1,
wherein the first vibration damping member has a natural frequency lower than a natural frequency of the housing.

4. The biological sound acquisition device according to claim 1,
wherein the second acceleration sensor is mechanically connected to the housing through a second vibration damping member.

5. The biological sound acquisition device according to claim 1, further comprising:
a first holder accommodating the first acceleration sensor, the first holder being in contact with a measurement object.

6. The biological sound acquisition device according to claim 1, further comprising:
a second holder accommodating the second acceleration sensor, the second holder being spaced apart from a measurement object.

7. The biological sound acquisition device according to claim 1, further comprising:
an acquisition unit for acquiring a difference between a detection signal of the first acceleration sensor and a detection signal of the second acceleration sensor.

8. A biological sound acquisition device comprising:
a housing;
a first vibration sensor disposed within the housing and mechanically connected to the housing through a first vibration damping member; and
a second vibration sensor disposed within the housing,
wherein a biological sound propagates to the first vibration sensor without propagating through the first vibration damping member, and
wherein the biological sound propagates to the second vibration sensor through the first vibration damping member.

* * * * *